United States Patent
Zerfas

(10) Patent No.: US 8,870,858 B2
(45) Date of Patent: Oct. 28, 2014

(54) METHODS AND APPARATUS RELATED TO A SIDE-FIRE ASSEMBLY THAT HAS AN OPTICAL GRATING

(75) Inventor: Jeffrey W. Zerfas, Bloomington, IN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 161 days.

(21) Appl. No.: 12/948,959

(22) Filed: Nov. 18, 2010

(65) Prior Publication Data

US 2011/0118715 A1    May 19, 2011

Related U.S. Application Data

(60) Provisional application No. 61/262,399, filed on Nov. 18, 2009.

(51) Int. Cl.
*A61B 18/18* (2006.01)
*G02B 23/24* (2006.01)
*A61B 18/22* (2006.01)
*A61B 18/20* (2006.01)

(52) U.S. Cl.
CPC ............ *A61B 18/22* (2013.01); *G02B 23/2423* (2013.01); *A61B 2018/2294* (2013.01); *A61B 2018/2025* (2013.01); *G02B 23/2469* (2013.01)
USPC .............................................. 606/15; 385/39

(58) Field of Classification Search
CPC ... A61B 18/22; A61B 1/0017; G02B 23/2423
USPC ....................................... 606/15, 16; 385/39
See application file for complete search history.

(56) References Cited

U.S. PATENT DOCUMENTS

| 4,445,892 | A | | 5/1984 | Hussein et al. |
| 5,586,982 | A | * | 12/1996 | Abela ............................ 606/28 |
| 5,591,161 | A | | 1/1997 | Negus et al. |
| 5,982,962 | A | * | 11/1999 | Koops et al. ................... 385/37 |

(Continued)

FOREIGN PATENT DOCUMENTS

| DE | 9413311 U1 | 11/1994 |
| EP | 0610991 A2 | 8/1994 |

(Continued)

OTHER PUBLICATIONS

PCT International Search Report and PCT Written Opinion from the International Searching Authority for corresponding PCT application PCT/US2010/057154 mailed Mar. 16, 2011 (16 pages total).

*Primary Examiner* — Lynsey Crandall
*Assistant Examiner* — Nathan J Jenness
(74) *Attorney, Agent, or Firm* — Bookoff McAndrews, PLLC

(57) ABSTRACT

An apparatus may include an optical fiber having an angled grating aligned along a plane non-normal to a longitudinal axis of a distal end portion of the optical fiber. The angled grating may be configured to redirect a first laser energy propagated within the optical fiber and incident on the angled grating to a direction offset from the longitudinal axis. The apparatus may also include a metallic cap coupled to the optical fiber. The metallic cap may have an inner surface configured to redirect a second laser energy incident on the inner surface along the direction offset from the longitudinal axis. The second laser energy being different than the first laser energy.

20 Claims, 6 Drawing Sheets

(56) References Cited

U.S. PATENT DOCUMENTS

| | | |
|---|---|---|
| 6,096,028 A | 8/2000 | Bahmanyar et al. |
| 6,296,608 B1 | 10/2001 | Daniels et al. |
| 6,398,778 B1 * | 6/2002 | Gu et al. .................. 606/15 |
| 7,169,140 B1 | 1/2007 | Kume |
| 7,306,588 B2 * | 12/2007 | Loeb et al. .................. 606/15 |
| 8,358,890 B2 | 1/2013 | Zerfas et al. |
| 2005/0075704 A1 | 4/2005 | Tu et al. |
| 2007/0179485 A1 | 8/2007 | Yeik et al. |
| 2011/0176770 A1 | 7/2011 | Zerfas et al. |
| 2011/0176772 A1 | 7/2011 | Hixon et al. |

FOREIGN PATENT DOCUMENTS

| | | |
|---|---|---|
| EP | 1072231 A1 | 1/2001 |
| WO | WO 01/08579 A1 | 2/2001 |
| WO | WO 2006/135701 A2 | 12/2006 |

\* cited by examiner

METHODS AND APPARATUS RELATED TO A SIDE-FIRE ASSEMBLY THAT HAS AN OPTICAL GRATING

CROSS-REFERENCE TO RELATED APPLICATIONS

The present application is related to, and claims priority from, U.S. Provisional Patent Application Ser. No. 61/262,399 filed on Nov. 18, 2009 which is incorporated herein by reference in its entirety.

BACKGROUND

Embodiments relate generally to optical medical devices, and, in particular, to side-fire optical fibers and methods for using such devices.

During some laser-based surgical procedures, a side-fire optical fiber can provide a medical practitioner with more control than a straight-firing optical fiber when applying laser energy to a treatment area. For example, laser energy can be emitted precisely towards a target area in a lateral direction via an angled surface of a side-fire optical fiber. Even if carefully manufactured using known manufacturing techniques, a side-fire optical fiber can be susceptible to, for example, overheating, inefficiencies due to undesirable laser energy leakage, and/or premature failure.

Thus, a need exists for methods and apparatus related to a side-fire optical fiber that can increase device longevity, increase laser energy transmission efficiency, reduce overheating, and/or increase patient safety.

SUMMARY

In one embodiment, an apparatus can include an optical fiber having an optical grating aligned along a plane non-normal to a longitudinal axis of a distal end portion of the optical fiber. The optical grating can be configured to redirect a first laser energy propagated within the optical fiber and incident on the optical grating to a direction offset from the longitudinal axis. The apparatus can also include a metallic cap coupled to the optical fiber. The metallic cap can have an inner surface configured to redirect a second laser energy incident on the inner optical grating along the direction offset from the longitudinal axis. The second laser energy being different than the first laser energy.

In one embodiment, a minimally-invasive medical device can include an optical fiber that has a distal end portion configured to be disposed within a body of a patient. An angled grating can be disposed within the distal end portion of the optical fiber. The angled grating can be configured to redirect laser energy propagated within the optical fiber and incident on the angled grating toward a tissue within the body of the patient.

In some embodiments, the laser energy can be redirected in a direction offset from a longitudinal axis of the distal end portion of the optical fiber. In some embodiments, the angled grating can be aligned along a plane non-normal to a longitudinal axis of the distal end portion of the optical fiber. In some embodiments, the angled grating can be a first angled grating aligned along a first plane, and the apparatus can also include a second angled grating aligned along a second plane non-parallel to the first plane.

In some embodiments, the laser energy can be from a first form of laser energy. The angled grating can be a first angled grating. The apparatus can also include a second angled grating disposed within the distal end portion of the optical fiber and configured to reflect laser energy from a second form of laser energy. In some embodiments, the optical fiber can be a single-mode optical fiber.

In some embodiments, the apparatus can also include a metallic cap coupled to the optical fiber and having an opening. The angled grating can be configured to redirect the laser energy toward the tissue through the opening of the metallic cap. In some embodiments, the optical fiber can have a germanium-doped core, and the angled grating can be embedded within the germanium-doped core. hi some embodiments, the angled grating can be a Bragg grating.

In another embodiment, an apparatus can include an optical fiber having an angled grating aligned along a plane non-normal to a longitudinal axis of a distal end portion of the optical fiber. The angled grating can be configured to redirect a first laser energy propagated within the optical fiber and incident on the angled grating to a direction offset from the longitudinal axis. A metallic cap can be coupled to the optical fiber. The metallic cap can have an inner surface configured to redirect a second laser energy incident on the inner surface along the direction offset from the longitudinal axis. The second laser energy can be different than the first laser energy.

In some embodiments, the optical fiber is configured such that the first laser energy can be propagated within a core of the optical fiber, the angled grating is substantially disposed within the core of the optical fiber. In some embodiments, the optical fiber is configured such that the angled grating can be aligned along a first plane. The optical fiber can have an angled grating aligned along a second plane non-parallel to the first plane.

In some embodiments, the angled grating is configured to redirect the first laser energy defined by electromagnetic radiation from a first spectral region of electromagnetic radiation. The angled grating is configured to redirect the second laser energy defined by electromagnetic radiation within a second spectral region of electromagnetic radiation different than the first spectral region of electromagnetic radiation.

In some embodiments, the first laser energy can be emitted from a first laser energy source. The second laser energy can be emitted from a second laser energy source different than the first laser energy source. In some embodiments, the optical fiber can be configured such that the first laser energy is within an ultraviolet spectral region of electromagnetic radiation. The optical fiber can be configured such that the second laser energy is within a visible spectral region of electromagnetic radiation.

In some embodiments, the metallic cap can have an opening aligned with the direction such that the first laser energy and the second laser energy are transmitted through the opening. In some embodiments, the apparatus can also include a silica cap coupled to a distal end of the optical fiber such that the silica cap can be disposed between the distal end of the optical fiber and at least a portion of the inner surface of the metallic cap.

In some embodiments, the optical fiber can have a core, and the apparatus can also include a silica cap coupled to a distal end of the optical fiber such that at least a portion of the silica cap is distal to the core of the optical fiber. In some embodiments, the optical fiber can be a single-mode optical fiber. In some embodiments, the optical fiber can be a multi-mode optical fiber. In some embodiments, the optical fiber can be a silica-based optical fiber. In some embodiments, the optical fiber can have a silica-based cladding layer disposed around a core of the optical fiber.

In yet another embodiment, a method can include inserting a distal end portion of an optical fiber into a patient's body. The distal end portion of the optical fiber can have an angled grating. The method can also include activating a laser source such that laser energy can be transmitted from the laser source toward the angled grating along a first portion of an optical path and can be reflected from the angled grating along a second portion of the optical path non-parallel to the first portion of the optical path.

In some embodiments, the laser source can be a first laser source and the laser energy can be a first laser energy. The activating associated with the first laser source can be performed at a first time. The method can also include activating a second laser source at a second time different from the first time such that a second laser energy can be transmitted along the first portion of the optical path and into a metallic cap disposed around the optical fiber. At least a portion of the second laser energy can be reflected from an interior portion of the metallic cap along at least a portion of the second portion of the optical path.

In some embodiments, the laser source can be a first laser source. The activating associated with the first laser source can be performed during a first time period. The method can also include activating a second laser source during a second time period before the first time period. At least a portion of the second time period can be mutually exclusive from the first time period.

In some embodiments, the laser source can be a treatment laser source and the laser energy can be a treatment laser energy. The method can also include activating an alignment laser source such that alignment laser energy can be transmitted from the alignment laser source along the second portion of the optical path.

DETAILED DESCRIPTION

Figure 1:
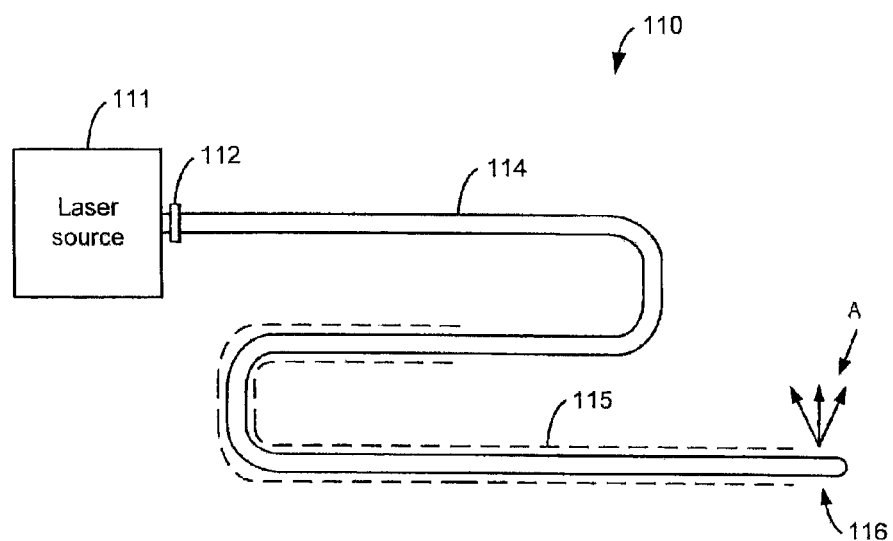
FIG. 1 is a schematic diagram of a side-fire system, according to an embodiment.

The devices and methods described herein are generally related to a side-fire member configured to treat an area within a body of a patient. One end of the side-fire member, the proximal end portion, can be coupled to a laser source while the other end of the side-fire member, the distal end portion, can be inserted into the patient's body to provide laser treatment. The side-fire member can be configured to transmit laser energy from the laser source to a treatment area (e.g., a target treatment area) that is disposed lateral to the distal end portion of the side-fire member. Specifically, an optical fiber (e.g., a fiber core of the optical fiber) within the side-fire member can have an angled grating non-normal and non-parallel to a longitudinal axis (or centerline) of a distal end portion of the optical fiber. The angled grating can define at least a portion of an interface (can be referred to as a reflective interface) configured to redirect laser energy propagated from within the optical fiber and incident on the interface to a direction offset (e.g., a lateral direction, a side-firing direction) from the longitudinal axis (or centerline) toward the target treatment area. The laser energy redirected via the interface can be referred to as lateral laser energy, redirected laser energy, or side-fired laser energy.

An optical fiber that has an angled grating configured to redirect laser energy in, for example, a lateral direction can be referred to as a side-fire optical fiber. The optical fiber and/or a laser source configured to emit (e.g., launch) laser energy into the optical fiber can be included in a side-fire system (also can be referred to as an optical fiber system). In some embodiments, the angled grating can be a type of optical grating and can be included in a distal end portion of the optical fiber. The side-fire member can have an optical fiber that has, for example, a fiber core, one or more cladding layers disposed around the fiber core, a buffer layer disposed around the cladding layer(s), and/or a jacket (disposed around the buffer layer). In some embodiments, the buffer layer can be referred to as a cladding layer.

At least a portion of an optical fiber that has an angled grating can be disposed within an outer cover and/or one or more capillary components (e.g., doped silica ($SiO_2$) capillary components, silica-based capillary components) that are coupled to (e.g., adhesively coupled to, fused to, heat-fused to) one another. Laser energy redirected by the angled grating can be transmitted through one or more of the capillary components. In some embodiments, the outer cover (e.g., a metallic cap, a polymer-based cap) can be coupled to the optical fiber and/or disposed outside of the capillary components and the optical fiber. The outer cover can be substantially opaque to a spectral region of electromagnetic radiation associated with the laser energy propagated within the optical fiber. In some embodiments, the outer cover can have a transmissive portion (e.g., a window or an opening) through which redirected laser energy can be transmitted. The optical fiber, the capillary components, and/or the outer cover can collectively define and can be referred to as a side-fire assembly of a side-fire system or as a laterally-firing end of a side-fire system. In some embodiments, the index of refraction of the capillary components disposed around the optical fiber can be defined at least in part by a doping concentration of a dopant (e.g., a fluorine dopant, a chlorine dopant, a rare-earth dopant, a germanium dopant, an alkali metal dopant, an alkali metal oxide dopant, etc.) within the capillary components. In some embodiments, any portion of the optical fiber can be optionally doped with any dopant that can be used to dope the capillary components, and vice versa.

In some embodiments, an angled grating can be defined within (e.g., formed from) a core portion of the optical fiber. For example, an angled grating configured to redirect laser energy in a lateral direction can be defined within (e.g., inscribed within, written within, inscribed within) an optical fiber using, for example, a laser (e.g., an ultraviolet (UV) laser), a photomask, interfering laser beams, and/or so forth. In some embodiments, the angled grating can be defined within a photosensitive optical fiber (e.g., a germanium-doped optical fiber). In some embodiments, the angled grating can be a Bragg grating.

In some embodiments, an angled grating can be a relatively small feature compared with a length of an optical fiber within a side-fire member. For example, in some embodiments, an angled grating can have a thickness of a few micrometers within an optical fiber that is several centimeters long. In some embodiments, the angled grating can be a portion (e.g., a thin slice) of the optical fiber that has an index of refraction that is different than an index of refraction of a majority portion (e.g., a bulk portion, a remaining portion of the fiber core) of the optical fiber. In some embodiments, an angled grating can be configured to substantially redirect a specified range of wavelengths (e.g., a contiguous range of wavelengths, a range of wavelengths that has at least one discontinuity) of electromagnetic radiation propagating within an optical fiber and incident on an interface defined by the angled grating. In some embodiments, the range of wavelengths can be centered about a particular wavelength (e.g., a wavelength associated with red light). Electromagnetic radiation having wavelengths outside of the specified range can be substantially transmitted through the angled grating. In some embodiments, electromagnetic radiation having wavelengths outside of the specified range can be substantially transmitted through the angled grating substantially without being redirected.

The devices and methods described herein can be used in treating symptoms related to, for example, an enlarged prostate gland, a condition known as Benign Prostatic Hyperplasia (BPH). BPH is a common condition in which the prostate becomes enlarged with aging. The prostate is a gland that is part of the male reproductive system. The prostate gland includes two lobes that are enclosed by an outer layer of tissue and is located below the bladder and surrounding the urethra, the canal through which urine passes out of the body. Prostate growth can occur in different types of tissue and can affect men differently. As a result of these differences, treatment varies in each case. No cure for BPH exists, and once the prostate begins to enlarge, it often continues, unless medical treatment is initiated.

Patients who develop symptoms associated with BPH generally require some form of treatment. When the prostate gland is mildly enlarged, research studies indicate that early treatment may not be needed because the symptoms can clear up without treatment in as many as one-third of cases. Instead of immediate treatment, regular checkups are recommended. Only if the condition presents a health risk, or the symptoms result in major discomfort or inconvenience to the patient, is treatment generally recommended. Current forms of treatment include drug treatment, minimally-invasive therapy, and surgical treatment. Drug treatment is not effective in all cases and a number of medical procedures have been developed to relieve BPH symptoms that are less invasive than conventional surgery.

While drug treatments and minimally-invasive procedures have proven helpful for some patients, many doctors still recommend surgical removal of the enlarged part of the prostate as the most appropriate long-term solution for patients with BPH. For the majority of cases that require surgery, a procedure known as Transurethral Resection of the Prostate (TURP) is used to relieve BPH symptoms. In this procedure, the medical practitioner inserts an instrument called a resectoscope into and through the urethra to remove the obstructing tissue. The resectoscope also provides irrigating fluids that carry away the removed tissue to the bladder.

More recently, laser-based surgical procedures employing side-fire optical fibers and high-power laser sources have been used to remove obstructing prostate tissue. In these procedures, a doctor passes the optical fiber through the urethra using a cystoscope, a specialized endoscope with a small camera on the end, and then delivers multiple bursts of laser energy to destroy some of the enlarged prostate tissue and to shrink the size of the prostate. Patients who undergo laser surgery usually do not require overnight hospitalization, and in most cases, the catheter is removed the same day or the morning following the procedure. Generally, less bleeding occurs with laser surgery and recovery times tend to be shorter than those of traditional procedures such as TURP surgery.

A common laser-based surgical procedure is Holmium Laser Enucleation of the Prostate (HoLEP). In this procedure, a holmium:YAG (Ho:YAG) laser source is used to remove obstructive prostate tissue. The Ho:YAG surgical laser is a solid-state, pulsed laser that emits light at a wavelength of approximately 2100 nanometers (nm) This wavelength of light is particularly useful for tissue ablation as it is strongly absorbed by water. An advantage of Ho:YAG laser sources is that they can be used for both tissue cutting and for coagulation. Another common laser surgery procedure is Holmium Laser Ablation of the Prostate (HoLAP), where a Ho:YAG laser source is used to vaporize obstructive prostate tissue. The decision whether to use HoLAP or HoLEP is based primarily on the size of the prostate. For example, ablation may be preferred when the prostate is smaller than 60 cubic centimeters (cc). Laser-based surgical procedures, such as HoLAP and HoLEP, are often preferred because they produce similar results to those obtained from TURP surgery while having fewer complications and requiring shorter hospital stay, shorter catheterization time, and shorter recovery time. In some embodiments, different types of laser sources, such as a helium-neon (HeNe) laser source, can be used during a medical procedure such as those described above.

In some embodiments, alignment laser energy can be launched into a side-fire member and used to align a side-fire assembly at a distal end portion of the side-fire member with a treatment area of a patient in a desirable fashion during an alignment phase of a medical procedure. Specifically, the angled grating of the side-fire assembly can be oriented (by an operator) in a specified fashion with respect to the treatment area based on the alignment laser energy so that treatment laser energy can later be redirected by the angled grating towards the treatment area. After the side-fire assembly has been aligned with the treatment area of the patient, treatment laser energy can be launched into the side-fire member and redirected towards the treatment area of the patient during a treatment phase of the medical procedure.

It is noted that, as used in this written description and the appended claims, the singular forms "a," "an" and "the" include plural referents unless the context clearly dictates otherwise. Thus, for example, the term "a wavelength" is intended to mean a single wavelength or a combination of wavelengths. Furthermore, the words "proximal" and "distal" refer to direction closer to and away from, respectively, an operator (e.g., a medical practitioner, a nurse, a technician, etc.) who can insert the medical device into the patient. Thus, for example, the optical fiber end inserted inside a patient's body would be the distal end of the optical fiber, while the optical fiber end outside a patient's body would be the proximal end of the optical fiber.

FIG. 1 is a schematic diagram of a side-fire system 110, according to an embodiment. The side-fire system 110 can include a laser source 111, an optical coupler 112, a side-fire member 114, and a side-fire assembly 116. The side-fire system 110 also includes a suitable catheter or endoscope 115 for inserting the side-fire assembly 116 into a patient's body.

The laser source 111 can be configured to generate laser energy that can be propagated within the side-fire member 114, for example, during a surgical procedure. The laser source 111 can include, for example, a HeNe laser source, a Ho:YAG laser source, a neodymium-doped:YAG (Nd:YAG) laser source, a Thulium laser source, a semiconductor laser diode, and/or a potassium-titanyl phosphate crystal (KTP) laser source. In some embodiments, more than one laser source (e.g., more than one type of laser source) can be used during a surgical procedure.

In some embodiments, the laser source 111 can also have a control module (not shown) configured to control (e.g., to set, to modify) a timing, a wavelength, and/or a power of laser energy emitted from the laser source 111. In some embodiments, the control module can also be configured to perform various functions such as laser selection, filtering, temperature compensation, and/or Q-switching The control module can be a hardware-based control module and/or a software-based control module that can include, for example, a processor and/or a memory.

The side-fire member 114 can be coupled to the laser source 111 through the optical coupler 112. The optical coupler 112 can be, for example, a Sub-Miniature A (SMA) connector. The proximal end of the side-fire member 114 can be configured to receive laser energy from the laser source 111, and the distal end of the side-fire member 114 can be configured to output the laser energy A through the side-fire assembly 116. The side-fire member 114 can include an optical fiber that has, for example, a fiber core, one or more cladding layers disposed around the fiber core, a buffer layer disposed around the cladding layer(s), and a jacket (disposed around the buffer layer).

In some embodiments, the fiber core can be made of a suitable material for the transmission of laser energy from the laser source 111. In some embodiments, for example, the fiber core can be made of silica with a low hydroxyl ($OH^-$) ion residual concentration. Laser energy wavelengths ranging from about 500 nm to about 2100 nm can be propagated within the fiber core during a surgical procedure. An example of low hydroxyl (low-OH) fibers used in medical devices is described in U.S. Pat. No. 7,169,140 to Kume, the disclosure of which is incorporated herein by reference in its entirety. The fiber core can be a multi-mode fiber core and can have a step or graded index profile. The fiber core can also be doped with a dopant (e.g., an amplifying dopant, a Germanium dopant). The cladding can be a single or a double cladding that can be made of a hard polymer or silica. The buffer can be made of a hard polymer or acrylate, for example. When the optical fiber includes a jacket, the jacket can be made of Tefzel®, for example, or can be made of other polymer-based substances.

The side-fire assembly 116 can include one or more optical gratings that can individually or collectively operate to redirect laser energy in a direction non-parallel (e.g., a lateral direction) to a longitudinal axis or a centerline of the distal end of the fiber core. The optical grating(s) can be non-normal to a longitudinal axis (or centerline) of a distal end portion of the optical fiber and can be referred to as an angled grating(s). The optical grating(s) can be included in, for example, the fiber core, one or more cladding layers about the fiber core, and/or a buffer layer (which can function as a cladding layer).

Although not shown, the optical grating(s) configured to redirect laser energy can be disposed within one or more capillary components at the side-fire assembly 116 of the side-fire member 114. The capillary components can be disposed outside of an optical fiber of the side-fire member 114. In some embodiments, the capillary components can be, for example, adhesively coupled to and/or heat-fused to one another. For example, a first capillary component can be heat-fused to a cladding layer of the optical fiber of the side-fire member 114. The first capillary component can define at least a portion of an enclosure. A second capillary component can be disposed outside of the first capillary component and heat-fused to the first capillary component. In some embodiments, an outer cover, such as a metal cap, can be coupled to an outer surface of the second capillary component. Because the second capillary component is disposed outside of the first capillary component, the second capillary component can be referred to as an outer capillary component and the first capillary component can be referred to as an inner capillary component. More details related to capillary components that can be fused to a fiber core of a side-fire member are described in U.S. Patent Application No. 61/262,040, filed on Nov. 18, 2009, entitled, "Methods and Apparatus related to a Distal End of a Side-Fire Optical Fiber having Multiple Capillary Components," and U.S. Patent Application No. 61/262,397, filed on Nov. 18, 2009, entitled, "Methods and Apparatus related to a Side-Fire Member having a Doped Silica Component," both of which are incorporated herein by reference in their entireties.

In some embodiments, the endoscope 115 can define one or more lumens (also can be referred to as working channels). In some embodiments, the endoscope 115 can include a single lumen that can receive therethrough various components such as the side-fire member 114. The endoscope 115 can have a proximal end configured to receive the side-fire assembly 116 of the side-fire member 114 and a distal end configured to be inserted into a patient's body for positioning the side-fire assembly 116 of the side-fire member 114 in an appropriate location for a laser-based surgical procedure. For example, to relieve symptoms associated with BPH, the endoscope 115 can be used to place the optical-fiber side-fire assembly 116 at or near the enlarged portion of the prostate gland. The endoscope 115 can include an elongate portion that can be sufficiently flexible (or rigid) to allow the elongate portion to be maneuvered within the body.

The endoscope 115 can also be configured to receive various medical devices or tools through one or more lumens of the endoscope, such as, for example, irrigation and/or suction devices, forceps, drills, snares, needles, etc. An example of such an endoscope with multiple lumens is described in U.S. Pat. No. 6,296,608 to Daniels et al., the disclosure of which is incorporated herein by reference in its entirety. In some embodiments, a fluid channel (not shown) is defined by the endoscope 115 and coupled at a proximal end to a fluid source (not shown). The fluid channel can be used to irrigate an interior of the patient's body during a laser-based surgical procedure. In some embodiments, an eyepiece (not shown) can be coupled to a proximal end portion of the endoscope 115, for example, and coupled to a proximal end portion of an optical fiber that can be disposed within a lumen of the endoscope 115. Such an embodiment allows a medical practitioner to view the interior of a patient's body through the eyepiece.

Figure 2:
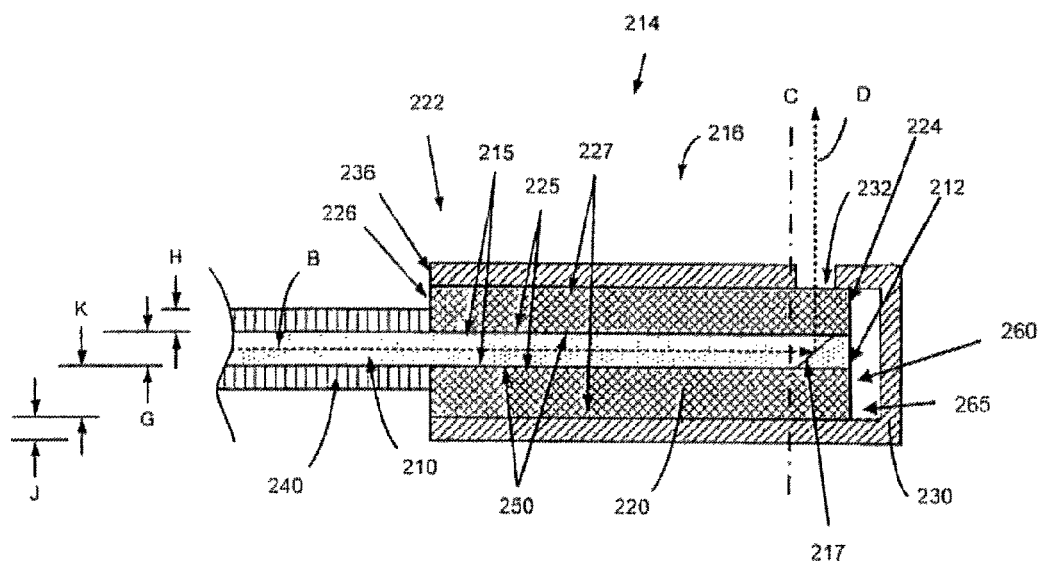
FIG. 2 is a side cross-sectional view of a side-fire assembly of a side-fire member that has an angled grating, according to an embodiment.

FIG. 2 is a side cross-sectional view of a side-fire assembly 216 of a side-fire member 214 that has an angled grating 217, according to an embodiment. The angled grating 217 is disposed inside of at least a portion of an optical fiber 210. An outer cover 230 (e.g., a metallic cover, a cover made of a polymer-based material) may be coupled to and disposed outside of a capillary component 220. The optical fiber 210 and the capillary component 220 can be made from a silica-based material (e.g., a pure (or substantially pure) silica material (without a dopant), a doped-silica material).

As shown in FIG. 2, laser energy B is propagated along a longitudinal axis (or centerline) of the optical fiber 210 of the side-fire member 214 and is redirected by the angled grating 217. The redirected laser energy D is transmitted through a portion of the capillary component 220 and an opening 232 defined by the outer cover 230. In other words, the laser energy B is transmitted within an optical path along the longitudinal axis (or centerline) of the optical fiber 210, and the redirected laser energy D is transmitted within an optical path that intersects the capillary component 220 and the opening 232. In some embodiments, the optical path(s) can include multiple segments. As shown in FIG. 2, a jacket layer 240 is disposed around at least a portion of the optical fiber 210.

Although not shown, the optical fiber 210 can have, for example, a fiber core, one or more cladding layers about the fiber core, and/or a buffer layer (e.g., a buffer layer disposed around a cladding layer). In some embodiments, at least a portion of the angled grating 217 can be included in the fiber core, one or more cladding layers, and/or a buffer layer (which can function as a cladding layer). For example, the angled grating 217 can be included in the fiber core, but not included in a cladding layer or a buffer layer. In some embodiments, the angled grating 217 can be included in only a portion of the fiber core. For example, in some embodiments, the angled surfaced 217 can be included in a bottom portion of a fiber core, but not in a top portion of a fiber core.

In some embodiments, the angled grating 217 can be a Bragg grating and/or can be made using laser energy. For example, the angled grating 217 can be produced from at least a portion of the optical fiber 210 that changes index of refraction when exposed to laser energy (e.g., curing laser energy that has a wavelength that is different than a wavelength of treatment laser energy and/or a wavelength of alignment laser energy). Specifically, at least a portion of the optical fiber 210 can be made of a germanium-doped material that is photosensitive and changes index of refraction with exposure to UV laser energy. The portion of the optical fiber 210 can be exposed to UV laser energy for a period of time to change an index of refraction of the portion of the optical fiber 210. The portion of the optical fiber 210 with the modified index of refraction can define the angled grating 217. In some embodiments, a level of change in the index of refraction of the optical fiber 210 can be defined based on, for example, an intensity and/or a duration of exposure of the photosensitive material to the laser energy. Accordingly, the index of refraction associated with the angled grating 217 can be defined based on the intensity and/or the duration of the exposure.

In some embodiments, the angled grating 217 can be defined using a multiple laser energy interference technique and/or a photomasking technique. In some embodiments, a photomask can be used to define a structure (e.g., a shape, a size) of the angled grating 217. In some embodiments, the angled grating 217 can be defined using a point-by-point laser writing technique. In some embodiments, the point-by-point laser writing technique can be performed using a relatively narrow beam of laser energy.

The capillary component 220 has an inner surface 225 that is heat-fused to an outer surface 215 of the optical fiber 210. Specifically, the inner surface 225 is heat-fused over substantially an entire area of the outer surface 215 of the optical fiber 210 that is disposed within the capillary component 220. Accordingly, the capillary component 220 can be heat-fused to a portion of the optical fiber 210 distal to the angled grating 217. Any portion of the outer surface 215 of the optical fiber 210 that is substantially parallel to, and disposed within the capillary component 220, can be heat-fused to the inner surface 225 of the capillary component 220.

In some embodiments, less than the entire area of the outer surface 215 of the optical fiber 210 can be heat-fused to the inner surface 225 of the capillary component 220. For example, in some embodiments, a portion of the outer surface 215 of the optical fiber 210 that is proximal to a plane C, which is at a proximal end of the angled grating 217 and substantially normal to a longitudinal axis (or centerline) of the optical fiber 210, can be heat-fused to the capillary component 220, and the portion of the outer surface 215 of the optical fiber 210 that is distal to the plane C may not heat-fused.

In some embodiments, multiple locations (e.g., at multiple random locations, at multiple locations in a pattern) along the outer surface 215 of the optical fiber 210 can be heat-fused to the inner surface 225 of the capillary component 220. For example, a portion of the outer surface 215 of the optical fiber 210 near a proximal end 222 of the side-fire assembly 216 and/or a portion of the outer surface 215 of the optical fiber 210 near the angled grating 217 can be heat-fused to the inner surface 225 of the capillary component 220. In some embodiments, for example, two or more circumferential portions (or non-circumferential portions) of the outer surface 215 can be heat-fused to the capillary component 220.

In some embodiments, the heat-fused portions do not continuously surround the optical fiber 210 and/or the capillary component 220. In other words, just a portion of the circumference (e.g., a top portion and/or a bottom portion) of the outer surface 215 of the optical fiber 210 can be heat-fused to the capillary component 220. The heat-fused area between the optical fiber 210 and the capillary component 220 can be sufficiently large to provide mechanical stability (e.g., resistance to shear forces) between the optical fiber 210 and the capillary component 220. In some embodiments, the capillary component 220 can be, for example, adhesively coupled to (e.g., adhesively coupled to using an epoxy) and/or mechanically coupled (e.g., mechanically coupled via a set screw and/or a press fit) to one or more portions of the optical fiber 210.

In some embodiments, the capillary component 220 and/or the optical fiber 210 can be made of various materials. For example, the capillary component 220 can be made from a doped-silica material (e.g., a fluorine-doped silica material) and the optical fiber 210 can be made from a substantially different doped-silica material (e.g., a substantially pure optical fiber core surrounded by a lightly doped fluorinated cladding). In some embodiments, for example, the capillary component 220 can be made of an undoped-silica material (e.g., substantially pure silica material) and a core portion of the optical fiber 210 can be made of a doped-silica material, and vice versa.

In some embodiments, the capillary component 220 can be made of a material that has an index of refraction that is different than an index of refraction of a material of the optical fiber 210 (e.g., a core portion and/or a cladding layer of the optical fiber 210). For example, the inner surface 225 of the capillary component 220 can have an index of refraction less than an index of refraction of the outer surface 215 of the optical fiber 210, and vice versa. In some embodiments, a portion of the laser energy B propagated within the optical fiber 210 and incident on the interface 250 can be totally or substantially totally internally reflected within the optical fiber 210 because an index of refraction on a side of the interface 250 that includes the capillary component 220 can be lower than an index of refraction of a side of the interface 250 that includes the optical fiber 210. In some embodiments, a portion of the laser energy B propagated within the optical fiber 210 and incident on the interface 250 can be transmitted (e.g., partially transmitted, totally transmitted) into the capillary component 220 because an index of refraction on the capillary component 220 side of the interface can be higher than an index of refraction of the optical fiber 210 side of the interface 250. If the optical fiber 210 has a cladding layer (not shown), a portion of the laser energy B propagated within the cladding layer and incident on the interface 250 can be totally (or substantially totally) internally reflected within the cladding layer.

The index of refraction of the optical fiber 210 and/or the capillary component 220 can be defined by, for example, a concentration of a dopant (e.g., fluorine). For example, an index of refraction of the capillary component 220 can be defined by a concentration of a fluorine dopant included in silica material used to make the capillary component 220. In some embodiments, the doping concentration of each of the optical fiber 210 and/or the capillary component 220 can be substantially uniform. In some embodiments, the doping concentration of the optical fiber 210 and/or the capillary component 220 can be non-uniform (e.g., can have a gradient). For example, the doping concentration at the inner surface 225 of the capillary component 220 can be lower than, for example, an outer surface 227 of the capillary component 220, or vice versa.

The outer cover 230 can be configured to keep stray laser energy (e.g., a portion of stray laser energy from laser energy B) from being transmitted in an undesirable direction out of the side-fire assembly 216 of the side-fire member 214. Accordingly, the outer cover 230 can be substantially opaque to the laser energy B and/or configured to reflect and/or absorb stray laser energy within (e.g., internal to) the side-fire assembly 216 of the side-fire member 214. The outer cover 230 can also provide protection (e.g., mechanical protection) to the side-fire assembly 216 of the side-fire member 214. The outer cover 230 can be, for example, adhesively coupled to (e.g., adhesively coupled to using an epoxy) and/or mechanically coupled (e.g., mechanically coupled via a set screw and/or a press fit) to the capillary component 220.

In some embodiments, the outer cover 230 can be made of a metallic material such as a surgical (e.g., medical) grade stainless steel, a plastic, or other material with like properties. In some instances, the outer cover 230 can be made of a ceramic material (e.g., alumina) because certain ceramics can have stable material characteristics at high-temperatures and/or have a high reflectance value at desirable operating wavelengths of the laser energy B.

As shown in FIG. 2, a distal end 212 of the optical fiber 210 is in contact with the outer cover 230. In some embodiments, the distal end 212 of the optical fiber 210 can be, for example, adhesively coupled to (e.g., adhesively coupled to using an epoxy) the outer cover 230. As shown in FIG. 2, the distal end 212 of the optical fiber 210 is aligned with a distal end 224 of the capillary component 220.

Although not shown, in some embodiments, the side-fire assembly 216 can be configured so that the distal end 212 of the optical fiber 210 is not aligned with the distal end 224 of the capillary component 220. In some embodiments, the distal end 212 of the optical fiber 210 can be proximal to the distal end 224 of the capillary component 220 so that a cavity is distal to the distal end 212 of the optical fiber 210. The cavity 260 distal to the distal end 212 can be defined by the distal end 212 of the optical fiber 210, the inner surface 225 of the capillary component 220, and the outer cover 230. In some embodiments, for example, as shown in FIG. 2, the cavity 260 distal to the distal end 212 can be filled with, for example, an epoxy 265. In some embodiments, the distal end 212 of the optical fiber 210 can be distal to the distal end 224 of the capillary component 220. In such embodiments, a cavity 260 distal to the distal end 224 of the capillary component 220 can be defined by the outer surface 215 of the optical fiber, the outer cover 230, and/or the distal end 224 of the capillary component. In some embodiments, the cavity 260 distal to the distal end 224 can be filled with, for example, an epoxy 265.

As shown in FIG. 2, the outer cover 230 has a proximal end 236 that is aligned with a proximal end 226 of the capillary component 220. Although not shown in FIG. 2, in some embodiments, the proximal end 236 of the outer cover 230 may not be aligned with the proximal end 226 of the capillary component 220. For example, in some embodiments, the outer cover 230 can extend over the proximal end 226 of the capillary component 220 can be coupled to the jacket layer 240. Although not shown in FIG. 2, in some embodiments, the proximal end 236 of the outer cover 230 can be adhesively coupled to the jacket layer 240 using, for example, an epoxy. Additional arrangements of outer covers within a side-fire assembly are described in U.S. Patent Application No. 61/262,404, filed on Nov. 18, 2009, entitled, "Methods and Apparatus related to a Distal End of a Side-Fire Optical Fiber having Multiple Capillary Components," which has been incorporated herein by reference in its entirety.

In some embodiments, rather than an opening 232, the outer cover 230 can include a transmissive material (not shown) through which the redirected laser energy D can be transmitted for surgical treatment. The transmissive material can be, for example, substantially transparent to a specified spectrum of electromagnetic radiation associated with the redirected laser energy D. The transmissive material can define, for example, a lens. In some embodiments, the transmissive material can be treated thermally, optically, mechanically, and/or chemically to define a desirable structural and/or optical characteristic. For example, the optically-transmissive material can be thermally treated during manufacturing using emissions from, for example, a carbon dioxide ($CO_2$) laser source. The transmissive material can be defined such that the redirected laser energy D can be delivered to a target area in a desirable fashion (e.g., delivered in a focused beam).

As shown in FIG. 2, the optical fiber 210 of the side-fire member 214 has an outer diameter G, for example, that can be between approximately a few micrometers (μm) (e.g., 20 μm) and hundreds of micrometers (e.g., 1500 μm). The jacket layer 240 around the optical fiber 210 can have a thickness H, for example, between a few micrometers (e.g., 5 μm) and hundreds of micrometers (e.g., 1500 μm). The capillary component 220 can have a thickness K of between, for example, approximately a few micrometers (e.g., 5 μm) and several millimeters (mm) (e.g., 2 mm). As shown in FIG. 2, the thickness K of the capillary component 220 is less than the thickness H of the jacket layer 240. The outer cover 230 can have a thickness J of a few micrometers (e.g., 5 μm) and several millimeters (mm) (e.g., 2 mm) Although not shown, in some embodiments, the outer cover 230 can be, for example, a low-profile cover (e.g., a coating or a sleeve).

Although not shown, in some embodiments, the optical fiber 210 can have a fiber core with an outer diameter, for example, between a few micrometers (μm) (e.g., 5 μm) and hundreds of micrometers (e.g., 1200 μm). The optical fiber 210 can have a cladding layer that is approximately 1 to 1.3 times greater than the outer diameter of the fiber core. In some embodiments, the optical fiber 210 can have a cladding layer with a thickness between, for example, approximately a few micrometers (μm) (e.g., 20 μm) and hundreds of micrometers (e.g., 1200 μm). The optical fiber 210 can also have a buffer layer with a thickness between, for example, approximately a few micrometers (μm) (e.g., 20 μm) and hundreds of micrometers (e.g., 1200 μm).

Although not shown in FIG. 2, in some embodiments, the angled grating 217 can be, for example, proximal to an angled surface at a distal end of the optical fiber 210 and/or a reflecting member such as a multilayer dielectric coating at a distal end of the optical fiber 210. The angled surface and/or the reflecting member can be configured to redirect laser energy propagated within the optical fiber 210 and incident on the angled surface and/or the reflecting member. More details related to examples of a reflecting member and/or angled surfaces are described in co-pending U.S. Patent Application No. 61/054,280, entitled, "Side-Firing Laser Fiber with Protective Tip and Related Methods," filed May 19, 2008, which is incorporated herein by reference in its entirety, and described in U.S. Patent Application No. 61/262,404, filed on Nov. 18, 2009, entitled, "Methods and Apparatus related to a Distal End of a Side-Fire Optical Fiber having Multiple Capillary Components," and U.S. Patent Application No. 61/262,397, filed on Nov. 18, 2009, entitled, "Methods and Apparatus related to a Side-Fire Member having a Doped Silica Component," both of which have been incorporated herein by reference in their entireties.

Figure 3:
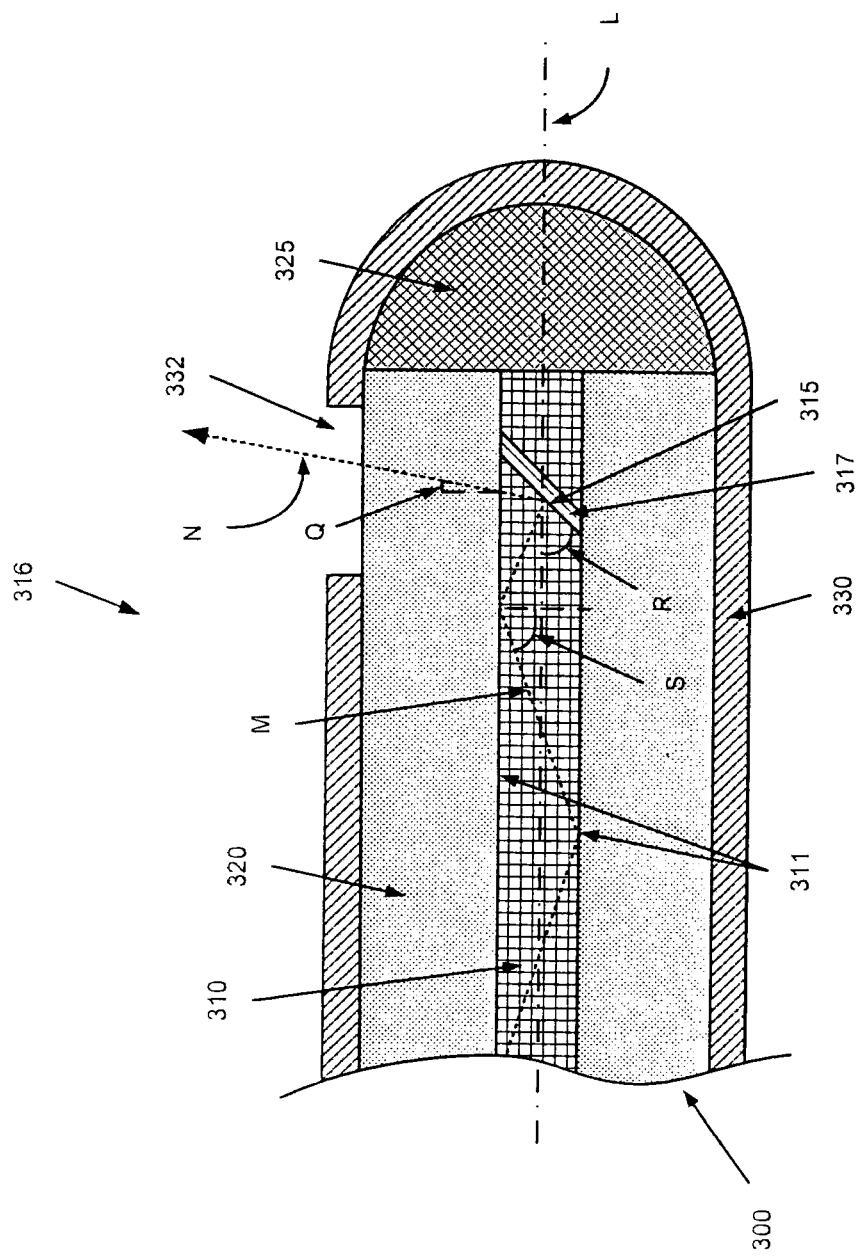
FIG. 3 is a schematic diagram that illustrates a side cross-sectional view of a side-fire assembly of a side-fire member, according to an embodiment.

FIG. 3 is a schematic diagram that illustrates a side cross-sectional view of a side-fire assembly 316 of a side-fire member, according to an embodiment. As shown in FIG. 3, an outer cover 330 is disposed around an optical fiber 300 that has a cladding layer 320 and a fiber core 310. The fiber core 310 has an angled grating 317 that is non-normal to a longitudinal axis L of the side-fire assembly 316. As shown in FIG. 3, the angled grating 317 and the fiber core 310 define an interface 315 configured to redirect laser energy M that is propagated from within the fiber core 310 and is incident on the interface 315. The redirected laser energy N is transmitted through the cladding layer 320 and out of an opening 332 within the outer cover 330.

In some embodiments, the fiber core 310 of the optical fiber 300 can have an outer diameter, for example, between a few micrometers (μm) (e.g., 5 μm) and hundreds of micrometers (e.g., 1200 μm). The cladding layer 312 of the optical fiber 300 can have an outer diameter that is many times (e.g., two times, three times) that of the fiber core 310. The outer cover 330 can have a thickness D of several micrometers to several millimeters. Although not shown, in some embodiments, the optical fiber 300 can include one or more additional cladding layers (in addition to cladding layer 320) and/or one or more buffer layers (e.g., an acrylate layer).

In some embodiments, the fiber core 310 can be a single mode laser fiber core. For example, in some embodiments, the fiber core 310 can be defined (e.g., can have an outer diameter defined) so that multiple spatial modes of laser energy cannot be propagated within the fiber core 310.

The fiber core 310 of the optical fiber 300 can be made of a pure silica (e.g., substantially pure silica with relatively few impurities) or can be made of a doped-silica material. For example, in some embodiments, the fiber core 310 can be made of a silicon-germanium (SiGe) material (also can be referred to as a germanium-doped material). In some embodiments, the cladding layer 320 of the optical fiber 300 can be made of a pure silica (e.g., substantially pure silica with few impurities) or can be made of a doped-silica material (e.g., fluorine-doped material). The outer cover 330 can be made of, for example, a metallic material such as a stainless steel and/or aluminum.

The cladding layer 320 can have an index of refraction that is less than an index of refraction of the fiber core 310. Accordingly, the laser energy M that is incident on an interface 311 defined by the cladding layer 320 and the fiber core 310 can be internally reflected within the fiber core 310 as shown in FIG. 3. Portions of laser energy (not shown) that leak (also referred to as stray laser energy) into the cladding layer 320 can be internally reflected from the outer cover 330 back towards the fiber core 310 and/or can be absorbed by the outer cover 330.

In some embodiments, the fiber core 310 can have a numerical aperture that is relatively high. Accordingly, a level of stray laser energy emitted from within the fiber core 310 and into the cladding layer 320 can be relatively small even if, for example, the cladding layer 320 and the fiber core 310 are made of materials that have similar indices of refraction.

As shown in FIG. 3, at least a portion of the redirected laser energy N is substantially or totally transmitted through at least a portion of the cladding layer 320. In other words, an optical path of the redirected laser energy N intersects at least a portion of the cladding layer 320. An angle of incidence Q (relative to a reference line normal to the interface 311) of the redirected laser energy N is sufficiently small that the redirected laser energy N is substantially or totally transmitted through the cladding layer 320.

As shown in FIG. 3, an angle of incidence S of the laser energy M propagated within the fiber core 310 (relative to a line normal to interface 311) is sufficiently large that the laser energy M is substantially or totally internally reflected within the fiber core 310. In some embodiments, the indices of refraction the fiber core 310 and the cladding layer 320, respectively, can be defined so that a specified range of the angles of incidence that will reflect the laser energy M within the fiber core 310 (or range of angles of incidence that will transmit laser energy M through the cladding layer 320) can be achieved.

An angle R of the angled grating 317 (and/or interface 315) relative to a longitudinal axis (or centerline) L can be defined (e.g., determined, selected, designed) based on at least one of several parameters. For example, the angle R can be defined based on the wavelength of the laser energy M (and/or redirected laser energy N), the exit or output location for the redirected laser energy N, anticipated angle of incidence of the laser energy M, and/or the optical properties of the cladding layer 320. In some embodiments, the optical properties of the interface 315 can also be used in determining an appropriate angle R for the angled grating 317.

As shown in FIG. 3, a cap 325 is disposed distal to the optical fiber 300 and within the outer cover 330. The cap 325 can be, for example, can be made of a silica-based material (e.g., a pure silica material, a doped-silica material) and/or a different material (e.g., an epoxy, a polymer-based material, a metal, a transparent material). In some embodiments, the cap 325 can be made of the same (or similar) material as the fiber core 310 and/or the cladding layer 320. In some embodiments, the cap 325 can be heat-fused to the optical fiber 300 (e.g., heat-fused to the fiber core 310 and/or the cladding layer 320). In some embodiments, the cap 325 can be adhesively coupled to (e.g., adhesively coupled via an epoxy) and/or mechanically coupled to any portion of the optical fiber 300 and/or any portion of the outer cover 330.

Figure 4A:
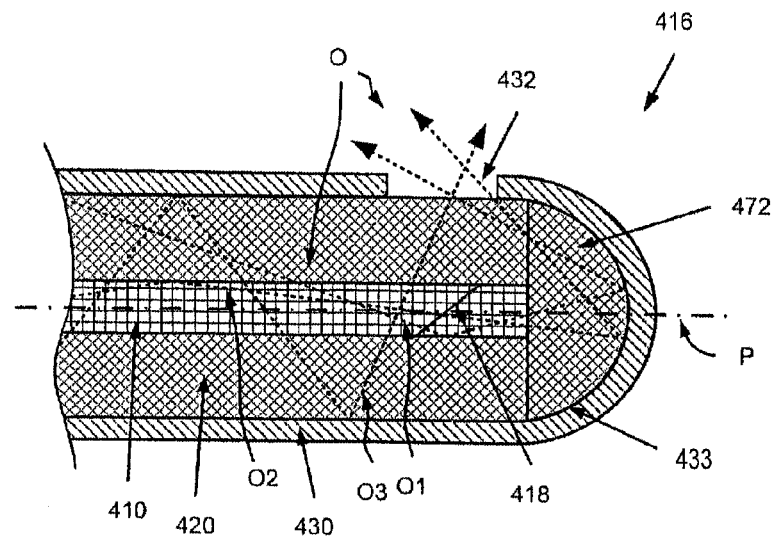
FIG. 4A is a schematic diagram that illustrates alignment laser energy being propagated within and redirected out of a side cross-sectional view of a side-fire assembly of a side-fire member, according to an embodiment.
Figure 4B:
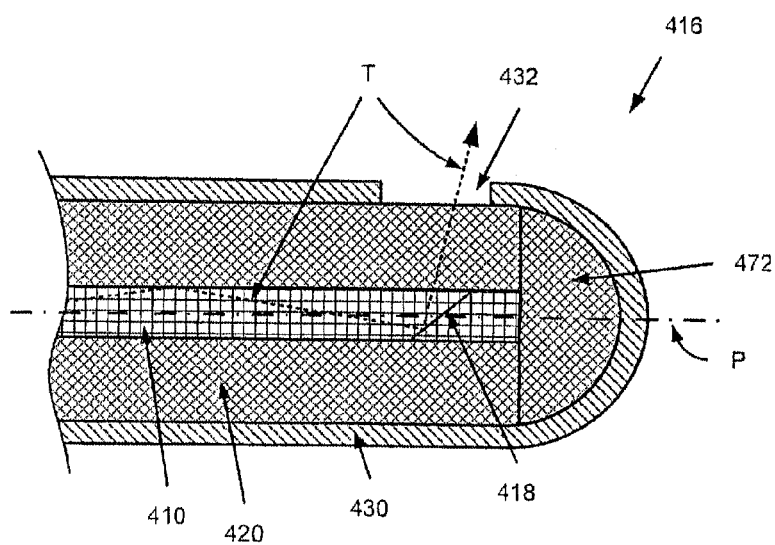
FIG. 4B is a schematic diagram that illustrates treatment laser energy being propagated within and redirected out of the side cross-sectional view of the side-fire assembly shown in FIG. 4A, according to an embodiment.

FIG. 4A is a schematic diagram that illustrates alignment laser energy 0 being propagated within and redirected out of a side cross-sectional view of a side-fire assembly 416 of a side-fire member, according to an embodiment. FIG. 4B is a schematic diagram that illustrates treatment laser energy T being propagated within and redirected out of the side cross-sectional view of the side-fire assembly 416 shown in FIG. 4A, according to an embodiment.

As shown in FIG. 4A and FIG. 4B, the side-fire assembly 416 includes a fiber core 410 surrounded by a cladding layer 420. An angled grating 418 is included in the fiber core 410. An outer cover 430 defines an opening 432, and is coupled to the cladding layer 420 and a cap 472.

The alignment laser energy O (shown in FIG. 4A) can be emitted from an alignment laser source (not shown) during alignment of the side-fire assembly 416 with a treatment area (e.g., a target area) during an alignment phase of a medical procedure. For example, the alignment laser energy O being redirected out of the opening 432, and visible to an operator of the side-fire assembly 416, can be used to align the opening 432 within the treatment area. After the side-fire assembly 416 has been aligned with the treatment area during the alignment phase, the treatment laser energy T (shown in FIG. 4B) can be emitted from an alignment laser source (not shown) during treatment of the treatment area during a treatment phase of the medical procedure.

As shown in FIG. 4A, the alignment laser energy O can be emitted into the side-fire assembly 416 so that the alignment laser energy O is reflected from an inner surface 433 of the outer cover 430. In some embodiments, the alignment laser energy O can be launched into the fiber core 410 and/or the cladding layer 420. The alignment laser energy O is propagated within the cladding layer 420 and/or through the fiber core 410. As shown in FIG. 4A, the alignment laser energy 0 has a portion O1 and a portion O2 (which is propagated within the fiber core 410) that are passed through (e.g., transmitted through) the angled grating 418. The angled grating 418 can be configured to allow transmission of laser energy associated with a range of wavelengths through the angled grating 418 without being reflected (e.g., substantially without being reflected or refracted). Because the portion O1 and the portion O2 are electromagnetic radiation within that range of wavelengths, portion O1 and portion O2 are transmitted through the angled grating 418 and reflected from the inner surface 433 of the outer cover 430. In some embodiments, the range of wavelengths of the alignment laser energy O can be centered about a specified wavelength (e.g., a wavelength associated with red light). As shown in FIG. 4A, an angle of incidence of the portion O3 at an interface between the cladding layer 420 and the core 410 is sufficiently large that the portion O3 passes through the interface between the cladding layer 420 and the core 410 without being reflected with the core 410.

As shown in FIG. 4B, the treatment laser energy T can be emitted into (e.g., launched into) and propagated within the fiber core 410. As shown in FIG. 4B, the treatment laser energy T is redirected by an interface defined in part by the angled grating 418 so that the laser energy T is transmitted through the opening 432 of the outer cover 430. The angled grating 418 can be configured so that the treatment laser energy T is redirected (e.g., substantially redirected, substantially reflected) at the angled grating 418. Even though the angled grating 418 is configured to allow transmission of (without redirection of) laser energy associated with the range of wavelengths associated with the alignment laser energy O, the angled grating 418 can be configured to redirect laser energy associated with a range of wavelengths associated with the treatment laser energy T. Accordingly, the range of wavelengths associated with the alignment laser energy O can be substantially different from (e.g., mutually exclusive from) the range of wavelengths associated with the treatment laser energy T. In some embodiments, the range of wavelengths of the treatment laser energy T can be centered about a specified wavelength (e.g., a wavelength associated with green light).

In some embodiments, the alignment laser energy O (shown in FIG. 4A) can be within a range of wavelengths overlapping with or substantially the same as a range of wavelengths of the treatment laser energy T (shown in FIG. 4B). If the range of wavelengths of the alignment laser energy O is overlapping with or substantially the same as the range of wavelengths of the treatment laser energy T, at least a portion of the alignment laser energy O can be reflected from the angled grating 418.

In some embodiments, the alignment laser energy O can be electromagnetic radiation transmitted at a lower intensity than the treatment laser energy T. In such instances, the alignment laser energy O can be used to align the side-fire assembly 416 with a treatment area without adversely affecting the treatment area and/or a non-treatment area during the alignment process. In some embodiments, the alignment laser energy O and/or the treatment laser energy T can be emitted for a specified period of time (e.g., for 5 seconds), pulsed during a medical procedure, and/or so forth.

In some embodiments, the alignment laser energy O can have at least a portion of wavelengths that are within a visible range of wavelengths (e.g., a range of wavelengths visible to a human) so that an operator can see the alignment laser energy O during an alignment phase. In some embodiments, the alignment laser energy O can have at least a portion of wavelengths that are within an invisible range of wavelengths (e.g., a range of wavelengths invisible to a human). In some embodiments, the treatment laser energy T can have a portion within a visible range of wavelengths and/or can have a portion within an invisible range of wavelengths.

In some embodiments, the alignment laser energy O (shown in FIG. 4A) and the treatment laser energy T (shown in FIG. 4B) can be emitted during mutually exclusive time periods. Although not shown, in some embodiments, the alignment laser energy O and the treatment laser energy T can be emitted during overlapping time periods. For example, the alignment laser energy O can be emitted into the side-fire assembly 416 during an alignment phase of a medical procedure. Later, during a treatment phase of the medical procedure, the treatment laser energy T and the alignment laser energy O can be emitted during at least a specified period of time during a treatment phase of the medical procedure. The alignment laser energy O can include visible light that can be emitted during the treatment phase of the medical procedure so that an operator can visually verify based on the alignment laser energy O that the treatment laser energy T (e.g., visible treatment laser energy, invisible treatment laser energy) is being properly emitted towards the treatment area (or a different treatment area that could be in close proximity to the treatment area).

In some embodiments, the side-fire assembly 416 can be configured so that the alignment laser energy O will be transmitted from the side-fire assembly 416 onto a specified surface area of a target (not shown) outside of the side-fire assembly 416 at a specified distance from the target. Similarly, in some embodiments, the side-fire assembly 416 can be configured so that the treatment laser energy T will be transmitted from the side-fire assembly 416 onto a specified surface area of a target (not shown) outside of the side-fire assembly 416 at a specified distance from the target. In some embodiments, a surface area covered by emitted alignment laser energy O and a surface area covered by emitted treatment laser energy T at a specified distance from a target (not shown) can be the same, or different. Although not shown, in some embodiments, multiple different types of alignment laser energy (e.g., alignment laser energy centered around different wavelengths) can be emitted from one or more alignment laser energy sources during, for example, an alignment phase of a medical procedure. Similarly, although not shown, in some embodiments, multiple different types of treatment laser energy (e.g., treatment laser energy centered around different wavelengths) can be emitted from one or more treatment laser energy sources during, for example, a treatment phase of a medical procedure.

Figure 5:
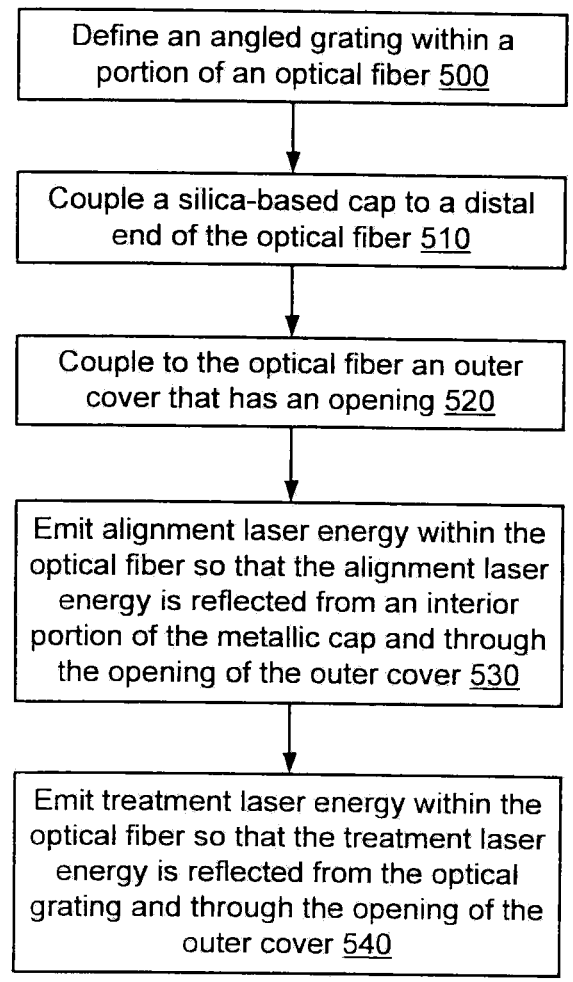
FIG. 5 is a schematic diagram that illustrates a method for producing and using a side-fire assembly, according to an embodiment.

FIG. 5 is a schematic diagram that illustrates a method for producing and using a side-fire assembly, according to an embodiment. As shown in FIG. 5, an angled grating is defined within a portion of an optical fiber, at 500. The optical fiber can have, for example, a germanium-doped fiber core and a cladding layer (e.g., a silica cladding layer, a fluorine-doped cladding layer). In some embodiments, the angled grating can be defined using, for example, laser energy. In some embodiments, multiple angled gratings can be defined within the optical fiber. In some embodiments, the angled grating can be configured to reflect electromagnetic radiation within a specified range of wavelengths.

A silica-based cap is coupled to a distal end of the optical fiber, at 510. The silica-based cap can be heat-fused to the end of the optical fiber in some embodiments. In some embodiments, the angled grating can be defined after the silica-based cap has been coupled to the distal end of the optical fiber. In some embodiments, the optical fiber does not have a silica-based cap. In some embodiments, a capillary component can be coupled to at least a portion of the optical fiber.

The optical fiber is coupled to an outer cover that has an opening, at 520. In some embodiments, the outer cover can be adhesively coupled to the optical fiber. In some embodiments, the opening can be aligned with the angled grating so that electromagnetic radiation that is reflected at the angled grating is transmitted through the opening.

Alignment laser energy is emitted within the optical fiber so that the alignment laser energy is reflected from an interior portion of the metallic cap and through the opening of the outer cover, at 530. The alignment laser energy can be emitted in response to an alignment laser source being activated. In some embodiments, the alignment laser energy can be within a range of wavelengths that are reflected by the angled surface. In some embodiments, the alignment laser energy can be within a range of wavelengths that are not reflected by (e.g., transmitted through) the angled surface. In some embodiments, electromagnetic radiation associated with the alignment laser energy can be intentionally emitted into (e.g., launched into) a cladding layer of the optical fiber.

Treatment laser energy is emitted within the optical fiber so that the treatment laser energy is reflected from the optical grating and through the opening of the outer cover, at 540. The treatment laser energy can be emitted in response to a treatment laser source being activated. In some embodiments, the treatment laser energy can be within a range of wavelengths that is overlapping with or mutually exclusive (e.g., substantially mutually exclusive from) the range of wavelengths associated with the alignment laser energy. In some embodiments, the side-fire assembly can be moved so that the angled surface has a specified orientation with respect to a treatment area based on emissions from the alignment laser energy during an alignment phase of a medical procedure so that the treatment laser energy can be reflected from the angled surface onto the treatment area in a desirable fashion.

Figure 6:
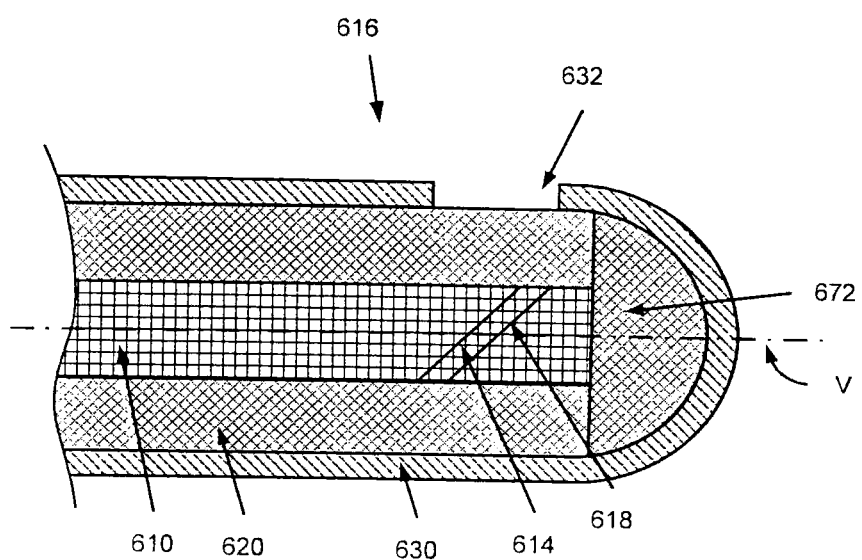
FIG. 6 is a schematic diagram that illustrates multiple angled gratings within a side-fire assembly, according to an embodiment.

FIG. 6 is a schematic diagram that illustrates multiple angled gratings within a side-fire assembly 616, according to an embodiment. Specifically, angled grating 614 and angled grating 618 are included in a fiber core 610 of the side-fire assembly 616. The fiber core 610 is disposed within a cladding layer 620. The fiber core 610 and the cladding layer 620 are coupled to (e.g., adhesively coupled to, heat-fused to) a cap 672. The cap 672 is made from the same material as the cladding layer 620. As shown in FIG. 6, the angled grating 614 and the angled grating 618 are configured to redirect laser energy through an opening 632 in an outer cover 630 that is coupled to the cladding layer 620 and the cap 672.

The angled grating 614 and the angled grating 618 can be configured to redirect laser energy of overlapping or mutually exclusive wavelengths. For example, angled grating 614 can be configured to redirect laser energy having a range of wavelengths centered around a first wavelength and angled grating 618 can be configured to redirect laser energy having a range of wavelengths centered around a second wavelength different than the first wavelength. The range of wavelengths centered around the first wavelength and the range of wavelengths centered around the second wavelength can be mutually exclusive (or substantially mutually exclusive). In some embodiments, for example, the angled grating 614 and the angled grating 618 can be configured to redirect laser energy within the same (or substantially same) range of wavelengths.

In some embodiments, the angled grating 614 can be configured to redirect alignment laser energy during an alignment phase of a medical procedure and the angled grating 618 can be configured to redirect treatment laser energy during a treatment phase of the medical procedure. In some embodiments, a range of wavelengths associated with the alignment laser energy can be different from (e.g., mutually exclusive from, substantially mutually exclusive from) and/or overlapping with a range of wavelengths associated with the treatment laser energy.

As shown in FIG. 6, the angled grating 614 and the angled grating 618 have similar orientations, or certain aspects of their orientations can be identical. For example, the angled grating 614 and the angled grating 618 can be substantially parallel with one another (but separate). Although not shown, in some embodiments, the angled grating 614 and the angled grating 618 can have different angles with respect to a longitudinal axis (or centerline) V of the side-fire assembly 616. For example, the angled grating 614 can be configured to redirect a portion of a laser energy in a first direction through opening 632 and the angled grating 618 can be configured to redirect another portion of the laser energy in a second direction (different from the first direction) through opening 632. Although not shown in some embodiments, the angled grating 614 and the angled grating 618 can be configured to redirect laser energy through different openings. For example, the angled grating 614 can be configured to redirect laser energy (e.g., treatment laser energy and/or alignment laser energy) through opening 632 and angled grating 618 can be oriented so that angled grating 618 can redirect laser energy (e.g., treatment laser energy and/or alignment laser energy) through an opening (not shown) mutually exclusive from opening 632.

In some embodiments, the angled grating 614, the angled grating 618, and/or another optical grating (e.g., an angled grating that is not shown in FIG. 6) can be configured to function as a spectral filter within the fiber core 610. For example, an optical grating (not shown) that is normal (e.g., substantially normal) to the longitudinal axis (or centerline) V and disposed within the fiber core 610 proximal to the angled grating 614 can be configured to reflect a specified range of wavelengths so that laser energy associated with the specified range of wavelengths will not (e.g., substantially will not) be propagated to (and incident on) the angled grating 614.

Although not shown, in some embodiments, the angled grating 614 and the angled grating 618 can have different shapes. For example, the angled grating 614 can have a different thickness than the angled grating 618. In some embodiments, at least a portion of the angled grating 614 and/or at least a portion of the angled grating 618 can extend into a cladding layer (or another layer that is not shown in FIG. 6). In some embodiments, the angled grating 614 and/or the angled grating 618 can have a cross-sectional area that is smaller than a cross-sectional area of the fiber core 610. For example, the angled grating 614 can have a cross-sectional area that is smaller than a cross-sectional area of the fiber core 610, and the angled grating 614 can have a center that is offset from the longitudinal axis (or centerline) V of the side-fire assembly 616. Accordingly, the angled grating 614 can be configured, in some embodiments, to redirect a spatial mode of laser energy that is different than a spatial mode of the laser energy redirected by the angled grating 618. In some embodiments, the angled grating 614 and/or the angled grating 618 can be non-planar (e.g., curved, bent).

Figure 7A:
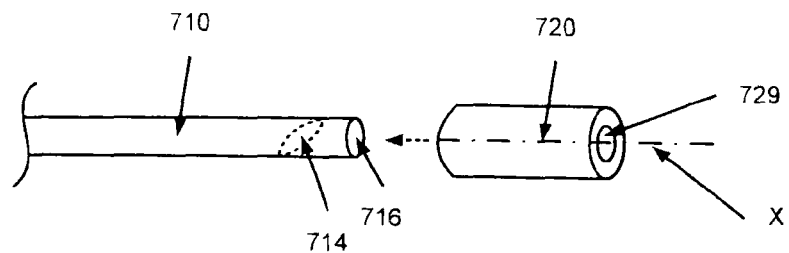
FIG. 7A is a schematic diagram that illustrates a doped-silica capillary component and an optical fiber before the doped-silica component is disposed over the optical fiber, according to an embodiment.
Figure 7B:
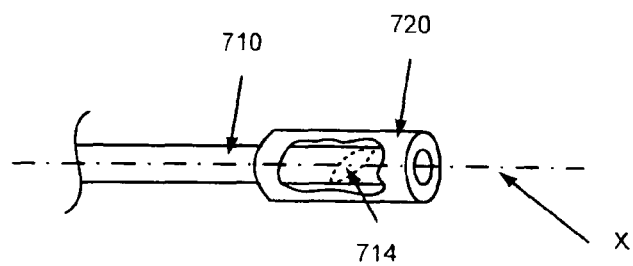
FIG. 7B is a schematic diagram that illustrates the doped-silica capillary component after being disposed over the optical fiber shown in FIG. 7A, according to an embodiment.

FIGS. 7A through 7D are schematic diagrams that collectively illustrate a method for producing a side-fire member, according to an embodiment. FIG. 7A is a schematic diagram that illustrates a doped-silica capillary component 720 and an optical fiber 710 before the doped-silica capillary component 720 is disposed over the optical fiber 710, according to an embodiment. FIG. 7B is a schematic diagram that illustrates the doped-silica capillary component 720 after being disposed (e.g., placed) over the optical fiber 710, according to an embodiment. As shown in FIG. 7A, an angled grating 714 is formed within optical fiber 710 before the doped-silica capillary component 720 is disposed over the optical fiber 710. The angled grating 714 is proximal to a distal end 716 of the optical fiber 710.

The doped-silica capillary component 720 has a bore 729 (e.g., a lumen) along a longitudinal axis (or centerline) X of the doped-silica capillary component 720. The bore 729 of the doped-silica capillary component 720 is in fluid communication with an opening at each end (along the longitudinal axis (or centerline) X) of the doped-silica capillary component 720. The doped-silica capillary component 720 can be cut from a length of a doped-silica tubular (e.g., cylindrical) pre-form (not shown). The doped-silica capillary component 720 component can be cut from the pre-form using, for example, a laser energy cutting instrument or a mechanical cutting instrument. The pre-form can be cut along a plane that is substantially normal to a longitudinal axis (or centerline) X of the pre-form.

In some embodiments, the doped-silica capillary component 720 can be uniformly or non-uniformly doped with, for example, fluorine and/or another suitable dopant. In some embodiments, the doped-silica capillary component 720 can be between 70 millimeters to 10 centimeters long. In some embodiments, the doped-silica tubular pre-form can have a doping concentration that is higher near an inner surface that defines the bore than at an outer surface of the pre-form.

In some embodiments, the size of the bore 729 can be increased before being disposed over the optical fiber 710. In some embodiments, the size of the bore 729 can be increased by removing a portion of a wall defining the bore 729 with, for example, a reaming device. An inner diameter of the bore 729 can be defined so that it is, for example, at least a few micrometers larger than an outer diameter of the optical fiber 710.

After the doped-silica capillary component 720 has been disposed over the optical fiber 710, the doped-silica capillary component 720 can be heat-fused to the optical fiber 710. In some embodiments, the doped-silica capillary component 720 and optical fiber 710 can be heated using, for example, a heating source (e.g., a torch, an electrical heating element, a laser source) until the doped-silica capillary component 720 and optical fiber 710 are fused. The doped-silica capillary component 720 and optical fiber 710 can be rotated about a longitudinal axis (or centerline) X of the optical fiber 710 while being heated.

Figure 7C:
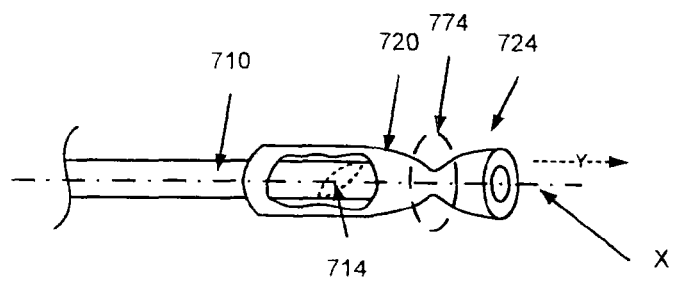
FIG. 7C is a schematic diagram that illustrates a distal end of the doped-silica capillary component shown in FIG. 7B being heated and pulled, according to an embodiment.

FIG. 7C is a schematic diagram that illustrates a distal end 724 of the doped-silica capillary component 720 being heated and pulled, according to an embodiment. The distal end 724 is being heated in a zone 774 while being pulled in direction Y until an enclosure 772 (shown in FIG. 7D) is formed. In other words, a force in direction Y (away from the angled grating 714) is applied on the distal end 724 while it is being heated. The doped-silica capillary component 720 can be heated until the doped-silica capillary component 720 softens and can be pulled. As the distal end 724 of the doped-silica capillary component 720 is heated and pulled, the doped-silica capillary component 720 plastically deforms until at least a portion of the distal end 724 is separated from the doped-silica capillary component 720 to define the shape of the doped-silica capillary component 720 shown in FIG. 7D. Although not shown, in some embodiments, the doped-silica capillary component 720 can be heated so that at least a portion of the doped-silica capillary component 720 is heat-fused to at least a portion of the distal end 716 of the optical fiber 710. The distal end 716 of the optical fiber 710 is shown in FIG. 7A.

In some embodiments, the heating and/or pulling discussed in connection with FIG. 7C are not performed coincidentally. For example, a portion of the distal end 724 can be heated before the distal end 724 is pulled. In some embodiments, the optical fiber 710 and doped-silica capillary component 720 can be rotated, for example, around the longitudinal axis (or centerline) X while being heated and/or pulled. In some embodiments, the heating associated with FIG. 7B (during fusing) and the heating associated with FIG. 7C can be performed using the same heating source and/or can be performed within the same heating cycle. In some embodiments, the heating associated with FIG. 7B and the heating associated with FIG. 7C can be performed separately (e.g., different space and time) using different heating sources.

Figure 7D:
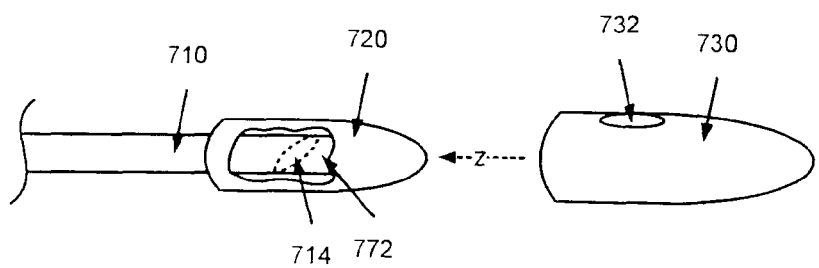
FIG. 7D is a schematic diagram that illustrates the doped-silica component heat-fused to the optical fiber shown in FIG. 7C and an outer cover, according to an embodiment

FIG. 7D is a schematic diagram that illustrates an outer cover 730 and a doped-silica capillary component 720 heat-fused to an optical fiber 720, according to an embodiment. An enclosure 772 is defined by the angled grating 714 and the doped-silica capillary component 720. As shown in 7D, the outer cover 730 can be moved in direction Z and coupled to the doped-silica capillary component 720. In some embodiments, at least a portion of a transmissive portion 732 is disposed within (e.g., intersects) an optical path of laser energy redirected by the angled grating 714.

While various embodiments have been described above, it should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described. For example, heat-fusing of multiple capillary component to an optical fiber that has an angled grating can be performed using multiple heat sources. Other embodiments of the invention will be apparent to those skilled in the art from consideration of the specification and practice of the invention disclosed herein. It is intended that the specification and examples be considered as exemplary only, with a true scope of the invention being indicated by the following claims.

What is claimed is:

1. A minimally-invasive medical device comprising:
an optical fiber having a distal end portion and an angled grating disposed at the distal end portion, the angled grating being configured to redirect laser energy propagated within the optical fiber and incident on the angled grating toward a tissue within the body of a patient;
a capillary component directly coupled to and surrounding the distal end portion of the optical fiber and extending distally beyond the grating;
a cover having a distal end enclosing a portion of the capillary component, the cover including a concavely rounded tip and a radial opening spaced from the optical fiber; and
an epoxy filling a cavity extending between a distalmost end of the capillary component, an outer surface of the distal end of the optical fiber, and the concavely rounded tip.

2. The device of claim 1, wherein the angled grating is aligned along a plane non-normal to a longitudinal axis of the distal end portion of the optical fiber.

3. The device of claim 1, wherein the angled grating is a first angled grating aligned along a first plane non-normal to a longitudinal axis of the distal end portion of the optical fiber, and the distal end portion of the optical fiber further includes a second angled grating aligned along a second plane non-parallel to the first plane.

4. The device of claim 1, wherein the angled grating is a first angled grating and the laser energy is a first form of laser energy, the device further including a second angled grating disposed within the distal end portion of the optical fiber, wherein the second angled grating is configured to reflect a second form of laser energy different from the first form of laser energy.

5. The device of claim 1, wherein the optical fiber includes a germanium-doped core, and the angled grating is embedded within the germanium-doped core.

6. The device of claim 1, wherein the angled grating is a Bragg grating.

7. The device of claim 1, wherein the angled grating is located proximal a distalmost end of the optical fiber.

8. The device of claim 1, wherein the epoxy fills the entire cavity between the distalmost end of the capillary component, an outer surface of the distal end of the optical fiber, and the concavely rounded.

9. The device of claim 1, wherein the radial opening terminates distally at a location proximal a distal end of the capillary component.

10. An apparatus, comprising:
an optical fiber, the optical fiber including an angled grating aligned along a plane non-normal to a longitudinal axis of a distal end portion of the optical fiber, wherein the angled grating is configured to redirect a first laser energy propagated within the optical fiber and incident on the angled grating to a direction offset from the longitudinal axis;
a capillary component surrounding the distal end portion of the optical fiber and extending distally beyond the grating;
a cover coupled to the optical fiber, the cover having a distal end distally enclosing the capillary component, a concavely rounded tip, and a radial opening spaced from the optical fiber, the cover also having an inner surface configured to redirect a second laser energy incident on the inner surface along the direction offset from the longitudinal axis, the second laser energy being different from the first laser energy; and
an epoxy filling a cavity extending between a distalmost end of the capillary component, an outer surface of the distal end of the optical fiber, and the concavely rounded tip.

11. The apparatus of claim 10, wherein the optical fiber is configured such that the first laser energy is propagated within a core of the optical fiber and the angled grating is disposed within the core of the optical fiber.

12. The apparatus of claim 10, wherein the optical fiber is configured such that the angled grating is aligned along a first plane, the optical fiber further including a second angled grating aligned along a second plane non-parallel to the first plane.

13. The apparatus of claim 10, wherein the angled grating is configured to redirect the first laser energy incident thereon and transmit the second laser energy incident thereon, the first laser energy being radiation from a first spectral region of an electromagnetic spectrum and the second laser energy being radiation from a second spectral region of the electromagnetic spectrum, the first spectral region being different from the second spectral region.

14. The apparatus of claim 13, wherein the first laser energy is emitted from a first laser energy source and the second laser energy is emitted from a second laser energy source different than the first laser energy source.

15. The apparatus of claim 13, wherein the first laser energy is radiation from an ultraviolet spectral region of the electromagnetic spectrum and the second laser energy is radiation from a visible spectral region of the electromagnetic spectrum.

16. The apparatus of claim 10, wherein the radial opening is aligned with the direction offset from the longitudinal axis such that the first laser energy and the second laser energy are transmitted through the opening.

17. The apparatus of claim 10, wherein the cover is a metallic cover, and the capillary component is coupled to a distal end portion of the optical fiber such that the capillary component is disposed between the distal end portion of the optical fiber and at least a portion of the inner surface of the metallic cover.

18. The device of claim 10, wherein the radial opening terminates distally at a location proximal a distal end of the capillary component.

19. A minimally-invasive medical device comprising:
an optical fiber having a distal end portion, and an angled grating disposed at the distal end portion, the angled grating being configured to redirect laser energy propagated within the optical fiber and incident on the angled grating toward a tissue within the body of a patient, a capillary component directly coupled to and surrounding the distal end portion of the optical fiber;

a cover directly coupled to and surrounding a portion of the capillary component, the cover including a concavely rounded tip and a radial opening; and an epoxy filling a cavity extending between a distalmost end of the capillary component, an outer surface of the distal end of the optical fiber, and the concavely rounded tip.

20. The device of claim 19, wherein the radial opening terminates distally at a location proximal a distal end of the capillary component.

* * * * *